United States Patent
Jung et al.

(10) Patent No.: US 10,512,878 B2
(45) Date of Patent: Dec. 24, 2019

(54) COMPLEX MALODOR REMOVING EQUIPMENT

(71) Applicants: Jae Ouk Jung, Yangsan-si (KR);
Myeong Sun Kim, Yangsan-si (KR);
Hyeong Jin Jeong, Yangsan-si (KR);
Yeo Jin Jeong, Geoje-si (KR)

(72) Inventors: Jae Ouk Jung, Yangsan-si (KR);
Myeong Sun Kim, Yangsan-si (KR);
Hyeong Jin Jeong, Yangsan-si (KR);
Yeo Jin Jeong, Geoje-si (KR); Yong Jun Jung, Busan (KR)

(73) Assignees: Jae Ouk Jung, Yangsan-si, Gyeongsangnam-do (KR); Myeong Sun Kim, Yangsan-si, Gyeongsangnam-do (KR); Hyeong Jin Jeong, Yangsan-si, Gyeongsangnam-do (KR); Yeo Jin Jeong, Geoje-si, Gyeongsangnam-do (KR)

( * ) Notice: Subject to any disclaimer, the term of this patent is extended or adjusted under 35 U.S.C. 154(b) by 141 days.

(21) Appl. No.: 15/769,740

(22) PCT Filed: Feb. 23, 2016

(86) PCT No.: PCT/KR2016/001734
§ 371 (c)(1),
(2) Date: Apr. 20, 2018

(87) PCT Pub. No.: WO2017/078224
PCT Pub. Date: May 11, 2017

(65) Prior Publication Data
US 2018/0311606 A1    Nov. 1, 2018

(30) Foreign Application Priority Data

Nov. 2, 2015 (KR) .................... 10-2015-0152995

(51) Int. Cl.
*B01D 47/00* (2006.01)
*A61L 9/00* (2006.01)
(Continued)

(52) U.S. Cl.
CPC .............. *B01D 47/021* (2013.01); *A61L 9/00* (2013.01); *A61L 9/145* (2013.01); *B01D 47/022* (2013.01);
(Continued)

(58) Field of Classification Search
CPC ......... A61L 9/00; A61L 9/145; B01D 47/022; B01D 47/021; B01D 47/027; B01D 47/10;
(Continued)

(56) References Cited

U.S. PATENT DOCUMENTS

| 3,969,479 A * | 7/1976 | Lonnes ................. B01D 53/34 423/210 |
| 4,994,245 A * | 2/1991 | Murray ................. B01D 53/84 423/238 |
| 2014/0202206 A1* | 7/2014 | Temple ................. B01D 53/75 62/617 |

FOREIGN PATENT DOCUMENTS

| JP | 54-21958 A | 2/1979 |
| JP | 55-13697 U | 1/1980 |

(Continued)

OTHER PUBLICATIONS

Office Action of Japan Patent Application No. 2018-519694 dated Feb. 19, 2019.
(Continued)

*Primary Examiner* — Sean E Conley
(74) *Attorney, Agent, or Firm* — Revolution IP, PLLC

(57) ABSTRACT

A complex malodor removing equipment includes: a neutralizing module which dissolves a portion of malodor-
(Continued)

causing substances, in malodorous gas introduced from malodor-producing equipment, in liquid water and removes same, which includes an acidity neutralizing module that introduces an alkaline substance from outside and removes an acidic malodor-causing substance from the malodor-causing substances, and an alkaline neutralizing module that introduces an acidic substance from outside and removes an alkaline malodor-causing substance from the malodor-causing substances, and which connects the acidity neutralizing module and the alkaline neutralizing module; and a balancing module which dissolves the remainder of the malodor-causing substances, in the malodorous gas introduced from the neutralizing module, in water and removes same, which includes an oxidation balancing module that introduces an oxidizing agent from outside and balances the malodor-causing substances, and a reduction balancing module that introduces a reducing agent from outside and balances the malodor-causing substances.

20 Claims, 8 Drawing Sheets

(51) Int. Cl.
| | | |
|---|---|---|
| B01D 53/58 | (2006.01) | |
| B01D 53/52 | (2006.01) | |
| B01D 53/68 | (2006.01) | |
| B01D 53/78 | (2006.01) | |
| B01D 53/72 | (2006.01) | |
| B01D 47/02 | (2006.01) | |
| B01D 47/10 | (2006.01) | |
| B01D 53/14 | (2006.01) | |
| B01D 53/44 | (2006.01) | |
| B01D 53/18 | (2006.01) | |
| B01D 53/48 | (2006.01) | |
| A61L 9/14 | (2006.01) | |

(52) U.S. Cl.
CPC ........... *B01D 47/027* (2013.01); *B01D 47/10* (2013.01); *B01D 53/1406* (2013.01); *B01D 53/18* (2013.01); *B01D 53/44* (2013.01); *B01D 53/48* (2013.01); *B01D 53/52* (2013.01); *B01D 53/58* (2013.01); *B01D 53/68* (2013.01); *B01D 53/72* (2013.01); *B01D 53/78* (2013.01); *A61L 2209/22* (2013.01); *B01D 2247/04* (2013.01); *B01D 2247/105* (2013.01); *B01D 2247/107* (2013.01); *B01D 2251/108* (2013.01); *B01D 2251/304* (2013.01); *B01D 2251/402* (2013.01); *B01D 2251/404* (2013.01); *B01D 2251/502* (2013.01); *B01D 2251/506* (2013.01); *B01D 2251/512* (2013.01); *B01D 2251/604* (2013.01); *B01D 2251/608* (2013.01); *B01D 2252/103* (2013.01); *B01D 2257/306* (2013.01); *B01D 2257/406* (2013.01); *B01D 2257/708* (2013.01); *B01D 2257/90* (2013.01); *B01D 2258/0258* (2013.01); *B01D 2258/0266* (2013.01); *B01D 2258/0275* (2013.01)

(58) Field of Classification Search
CPC .... B01D 53/1406; B01D 53/18; B01D 53/44; B01D 53/48; B01D 53/52; B01D 53/58; B01D 53/68; B01D 53/72; B01D 53/78
See application file for complete search history.

(56) References Cited

FOREIGN PATENT DOCUMENTS

| | | |
|---|---|---|
| JP | 56-26530 A | 3/1981 |
| JP | 56-141814 A | 11/1981 |
| JP | 3132698 U | 5/2007 |
| JP | 2015-44179 A | 3/2015 |
| KR | 10-0794208 B1 | 1/2008 |
| KR | 10-0901300 B1 | 6/2009 |
| KR | 10-0984387 B1 | 9/2010 |
| KR | 10-1001155 B1 | 12/2010 |
| KR | 10-1183665 B1 | 9/2012 |

OTHER PUBLICATIONS

International Search Report for PCT/KR2016/001734 dated Aug. 2, 2016 from Korean Intellectual Property Office.

* cited by examiner

COMPLEX MALODOR REMOVING EQUIPMENT

TECHNICAL FIELD

The present invention relates to complex malodor removing equipment, and more particularly, to complex malodor removing equipment that is capable of effectively removing various and complex malodor discharged from malodor-producing equipment.

BACKGROUND ART

In general, malodor is generated in natural malodor-producing sources, such as proteolysis caused by microorganism or unique smell of a material itself, and artificial malodor-producing sources, such as various types of business places. Among them, the artificial malodor-producing sources include sewage treatment plants, waste water treatment plants, night soil treatment plants, livestock excretions treatment plants, food wastes treatment plants, livestock production facility, landfill, incineration facility, and the like. In addition, malodor is generated in mobile contamination sources such as a vehicle, a truck, and the like, and construction sites, garbage gathering plants, an individual house, and the like.

Meanwhile, in view of main malodor-causing substances according to malodor-producing sources, hydrogen sulfide and methyl mercaptan are mainly generated in livestock production facility, night soil treatment plants, livestock excretions treatment plants, sewage treatment plants, and the like, and hydrocarbon such as benzene, toluene, styrene, and xylene, and aldehyde and ester-based materials are mainly generated due to an organic solvent used in paint manufacturing, stamp facility, printing and ink-manufacturing facility. Also, chlorine and hydrogen chloride are mainly discharged from fertilizer-manufacturing facility and incineration facility, and amines are mainly discharged from food-manufacturing facility, and trichloroethylene and tetrachloroethylene are mainly discharged from dry cleaning and washing facility, and fatty acids, aldehyde, and sulfur compounds are mainly discharged from food wastes treatment plants and composting facility.

However, a malodor removing apparatus according to the related art is limited to removing a particular portion of malodor-causing substances from malodor-producing sources. Thus, malodor cannot be effectively removed from various and complex malodor-causing substances discharged from, in particular, food wastes.

Further, the malodor removing apparatus according to the related art has low reactivity and thus introduces an excessive amount of medicine, which causes generation of malodor in post facility due to medicine.

DETAILED DESCRIPTION OF THE INVENTION

Technical Problem

The present invention provides complex malodor removing equipment that is capable of effectively removing various and complex malodor discharged from malodor-producing equipment and removing malodor caused by excessively-introduced treatment liquid.

Technical Solution

According to an aspect of the present invention, there is provided complex malodor removing equipment including: a neutralizing module which dissolves a portion of malodor-causing substances, in malodorous gas introduced from malodor-producing equipment, in liquid water and removes same, which includes an acidity neutralizing module that introduces an alkaline substance from outside and removes an acidic malodor-causing substance from the malodor-causing substances in order to neutralize same, and an alkaline neutralizing module that introduces an acidic substance from outside and removes an alkaline malodor-causing substance from the malodor-causing substances in order to neutralize same, and which connects the acidity neutralizing module and the alkaline neutralizing module in response to the malodorous gas and operates the acidity neutralizing module and the alkaline neutralizing module; and a balancing module which dissolves the remainder of the malodor-causing substances, in the malodorous gas introduced from the neutralizing module, in water and removes same, which includes an oxidation balancing module that introduces an oxidizing agent from outside and balances the malodor-causing substances in order to oxidize same, and a reduction balancing module that introduces a reducing agent from outside and balances the malodor-causing substances in order to reduce same, and which connects the oxidation balancing module and the reduction balancing module in response to the malodorous gas and operates the oxidation balancing module and the reduction balancing module.

Effects of the Invention

Complex malodor removing equipment according to the present invention provides the following effects.

First, a neutralizing module and a balancing module are provided so that various and complex malodor-causing substances generated from malodor-producing sources can be effectively removed through a plurality of malodor treating units comprised of various treatment liquid components.

Second, malodor-causing substances caused by an excessively-introduced oxidizing agent are removed so that finally-discharged malodor-causing substances can be effectively removed.

Third, deodorizing effects of malodorous gas can be further improved through an atomizing apparatus in which the malodorous gas is sprayed and refined under water, and furthermore, the usage amount of various medicines can be precisely adjusted and quantified, and oxygen in the air can be used as the oxidizing agent so that the usage amount of medicine can be reduced.

Fourth, in addition to deodorizing of the malodorous gas, water including malodor-causing substances dissolved therein is neutralized to weakly toxic components through the malodor treating units so that treatment of water can be simplified.

Fifth, treatment liquid is premixed with water and then is supplied into a storage space and is re-circulated so that the treatment liquid and water are uniformly mixed with each other and a liquid property change of water can be more effectively promoted.

MODE OF THE INVENTION

Hereinafter, exemplary embodiments of the present invention will be described in detail with reference to the accompanying drawings.

Figure 1:
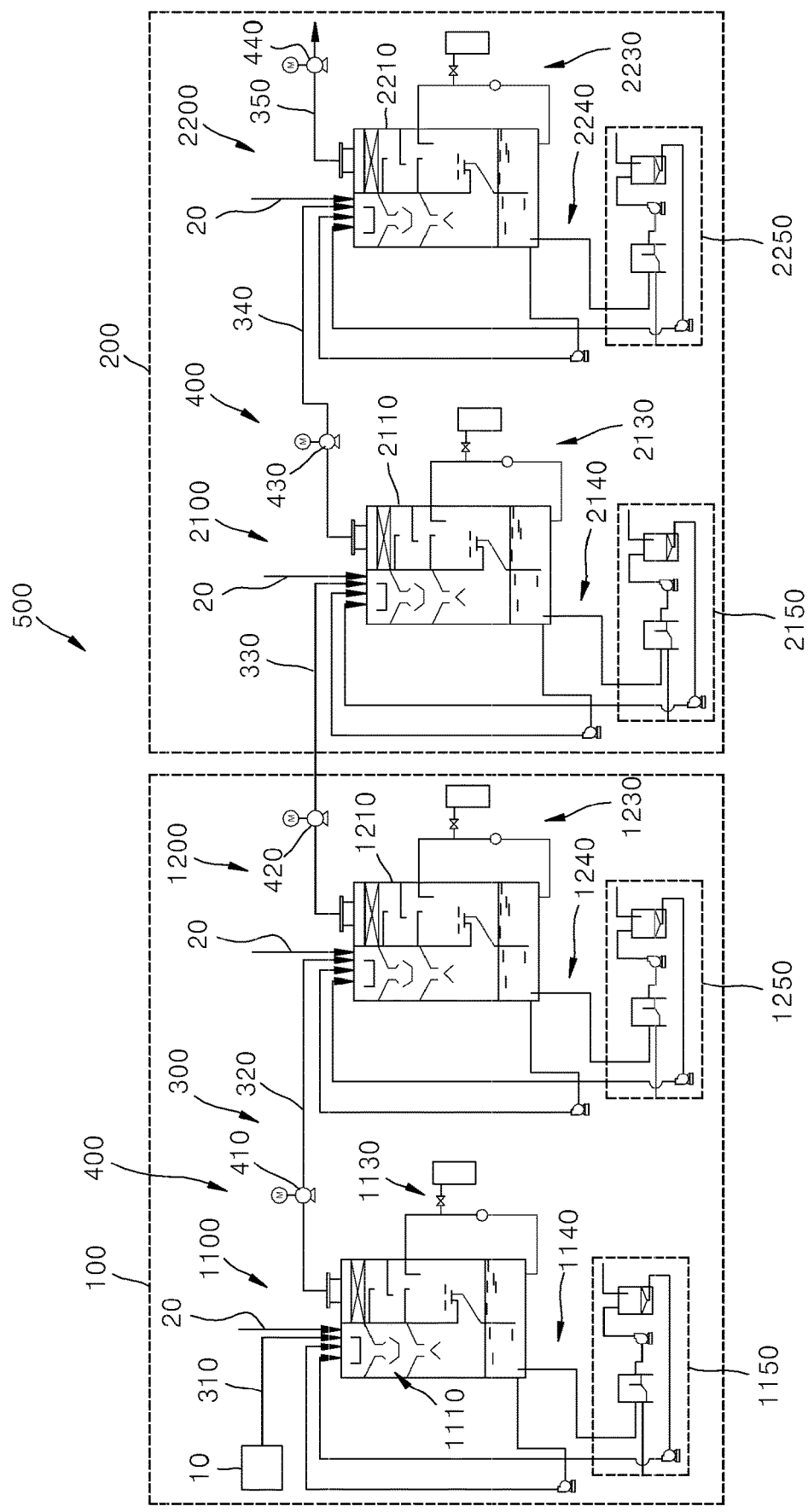
FIG. 1 is a view of a configuration of complex malodor removing equipment according to an embodiment of the present invention.
Figure 2:
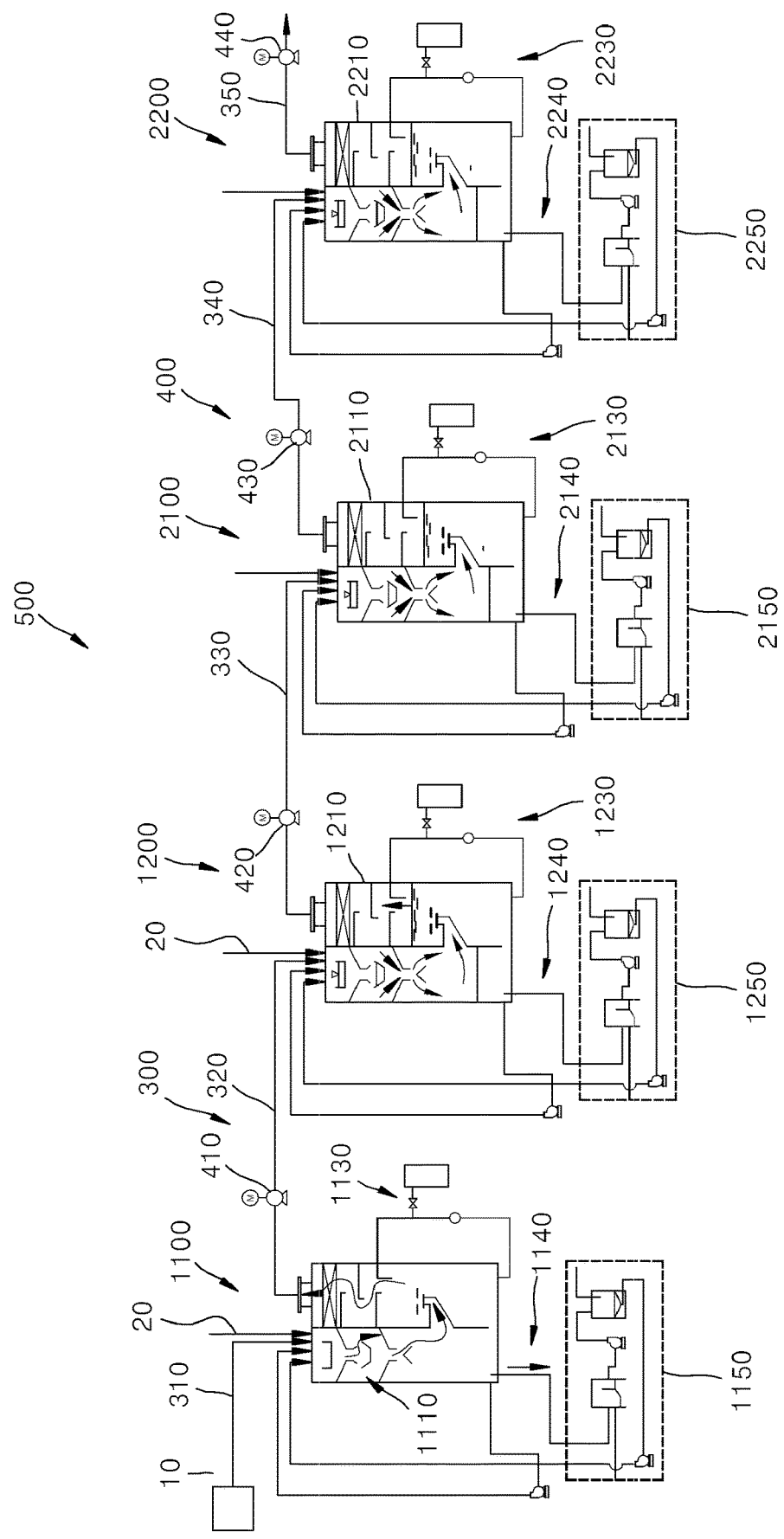
FIG. 2 is a view of a configuration of an operating state of the complex malodor removing equipment of FIG. 1.

First, referring to FIGS. 1 and 2, complex malodor removing equipment 500 according to an embodiment of the present invention includes a neutralizing module 100, a balancing module 200, a gas line 300, and a suction fan 400.

The neutralizing module 100 dissolves a portion of malodor-causing substances in malodour gas introduced from malodor-producing equipment 10 in water, removes the same, and includes an acidity neutralizing module 1100 and an alkaline neutralizing module 1200.

The acidity neutralizing module 1100 neutralizes an acidic malodor-causing substance, such as hydrogen sulphide in the malodorous gas, introduces an alkaline substance from outside so as to neutralize water in a storage space in which the acidic malodor-causing substance is dissolved and which has acidity, and removes the same.

The alkaline neutralizing module 1200 neutralizes an alkaline malodor-causing substance, such as ammonia or trimethylamine in the malodorous gas, introduces an acidic substance from outside so as to neutralize water in a storage space in which the alkaline malodor-causing substance is dissolved and which has alkalinity, and removes the same.

Meanwhile, the neutralizing module 100 serially-connects the acidity neutralizing module 1100 to the alkaline neutralizing module 1200 in response to the malodorous gas so that the malodorous gas passes through the acidity neutralizing module 1100 and the alkaline neutralizing module 1200 sequentially and the malodor-causing substances can be removed.

Preferably, the neutralizing module 100 serially-connects the acidity neutralizing module 1100 to the alkaline neutralizing module 1200 sequentially in the order of the acidity neutralizing module 1100 and the alkaline neutralizing module 1200. This is because the malodorous gas generally has content in the order of alkaline malodor, acidic malodor, and neutral malodor as malodor-causing substances. However, this is an exemplary embodiment, and the arrangement order of malodor treating units may be differently changed according to malodor-causing substances and the type of malodorous gas caused thereby.

The balancing module 200 dissolves the remainder of the malodour-causing substances in the malodorous gas introduced from the neutralizing module 100 in water, removes the same, and includes an oxidation balancing module 2100 and a reduction balancing module 2200.

The oxidation balancing module 2100 introduces an oxidizing agent from outside and neutralizes the same so as to oxidize and decompose water in which malodor-causing substances, such as acetaldehyde, methyl sulphide, dimethyl disulphide, methyl mercaptan, in the malodorous gas are dissolved.

Here, the oxidation balancing module 2100 may remove malodor-causing substances that cannot be removed by water or a neutralizing agent, using the oxidizing agent. The malodor-causing substances are odorless substances due to an oxidation reaction between oxygen and chlorine included in the treatment liquid and the malodor-causing substances and is fixed within a treatment medicine. Here, the oxidizing agent may cause a strong oxidation action with respect to hypochlorous acid (HClO), and deodorizing caused by hypochlorite soda having excellent handling and economic feasibility is preferable. This is an exemplary embodiment, and components that can achieve the above objectives, such as sulphide including hydrogen sulphide, methyl mercaptan, methyl sulphide, and dimethyl disulphide, ammonia, or trimethylamine may be applied in various ways.

The reduction balancing module 2200 removes the malodor-causing substances that are not properly removed by the above-described neutralizing module 100 and oxidation balancing module 2100, using a reducing agent so that deodorizing effects of the malodorous gas can be improved. That is, the reduction balancing module 2200 introduces the reducing agent from outside in water in which the malodor-causing substances that are not properly removed by a neutralizing agent or oxidizing agent of the above-described neutralizing module 100 and oxidation balancing module 2100 are dissolved, and reduces the same, thereby removing the malodor-causing substances.

In this way, the reduction balancing module 2200 reduces the above-described malodor-causing substances and removes the same, and also removes malodor caused by the oxidizing agent excessively introduced in the oxidation balancing module 2100. That is, the reduction balancing module 2200 removes malodor caused by hypochlorite ion (ClO) gas generated in the oxidizing agent excessively introduced in the above-described neutralizing module 100 and oxidation balancing module 2100. First, the oxidizing agent is excessively introduced, because the concentration of introduced malodor is not constant and substantially it is difficult to introduce an accurate amount of oxidizing agent. Thus, gas phase substances that are weak to an oxidation reaction exist, and malodor occurs. Thus, the reduction balancing module 2200 reduces the malodor-causing substances generated due to the above-described oxidizing agent and removes the same.

Here, the balancing module 200 serially-connects the oxidation balancing module 2100 to the reduction balancing module 2200 in response to the malodorous gas so that the malodor-causing substances can be removed. Preferably, the balancing module 200 serially-connects the oxidation balancing module 2100 to the reduction balancing module 2200 sequentially in the order of the oxidation balancing module 2100 and the reduction balancing module 2200.

Meanwhile, the complex malodor removing equipment 500 may operate the neutralizing module 100 and the balancing module 200 selectively in response to the malodorous gas. That is, the complex malodor removing equipment 500 may selectively operate the acidity neutralizing module 1100, the alkaline neutralizing module 1200, the oxidation balancing module 2100, and the reduction balancing module 2200, respectively. As illustrated, the complex malodor removing equipment 500 may stop an operation of the acidity neutralizing module 1100 and may operate only the other, alkaline neutralizing module 1200 and the balancing module 200 in response to components of the malodor-causing substances. Here, the operation of the acidity neutralizing module 1100 is stopped such that the malodor-causing substances in the malodorous gas cannot be dissolved in water. However, because the malodorous gas passes through elements such as a shielding plate 1171 and an eliminator 1172 that will be described later, refinement of the malodorous gas and collecting of moisture may be performed.

The gas line 300 is connected to and communicates with the neutralizing module 100 and the balancing module 200, respectively, so that the malodorous gas can flow into the gas line 300, can pass through the neutralizing module 100 and the balancing module 200 and can be discharged.

In detail, the gas line 300 includes a supply line 310 through which the malodorous gas is introduced from the malodor-producing equipment 10 and which supplies the malodorous gas to the neutralizing module 100, a first gas line 320 that connects the acidity neutralizing module 1100 and the alkaline neutralizing module 1200 within the neutralizing module 100 to each other, a second gas line 330 that connects the neutralizing module 100 to the balancing module 200, a third gas line 340 that connects the acidity balancing module 2100 and the reduction balancing module 2200 within the balancing module 200 to each other, and a discharge line 350, which is connected to a discharge port of the balancing module 200 and through which the treated malodorous gas is discharged to the outside.

The suction fan 400 is provided on the gas line 300, suctions the malodorous gas within the neutralizing module 100 and the balancing module 200, flows the same, and allows the inside of the neutralizing module 100 and the balancing module 200 to be in a negative (−) pressure state.

Here, the suction fan 400 includes a first suction fan 410 installed on the first gas line 320, a second suction fan 420 installed on the second gas line 330, a third suction fan 430 installed on the third gas line 340, and a fourth suction fan 440 installed on the discharge line 350, as illustrated, so that the suction fan 400 can be installed on the first gas line 320, the second gas line 330, the third gas line 340 and the discharge line 350, respectively.

Figure 3:
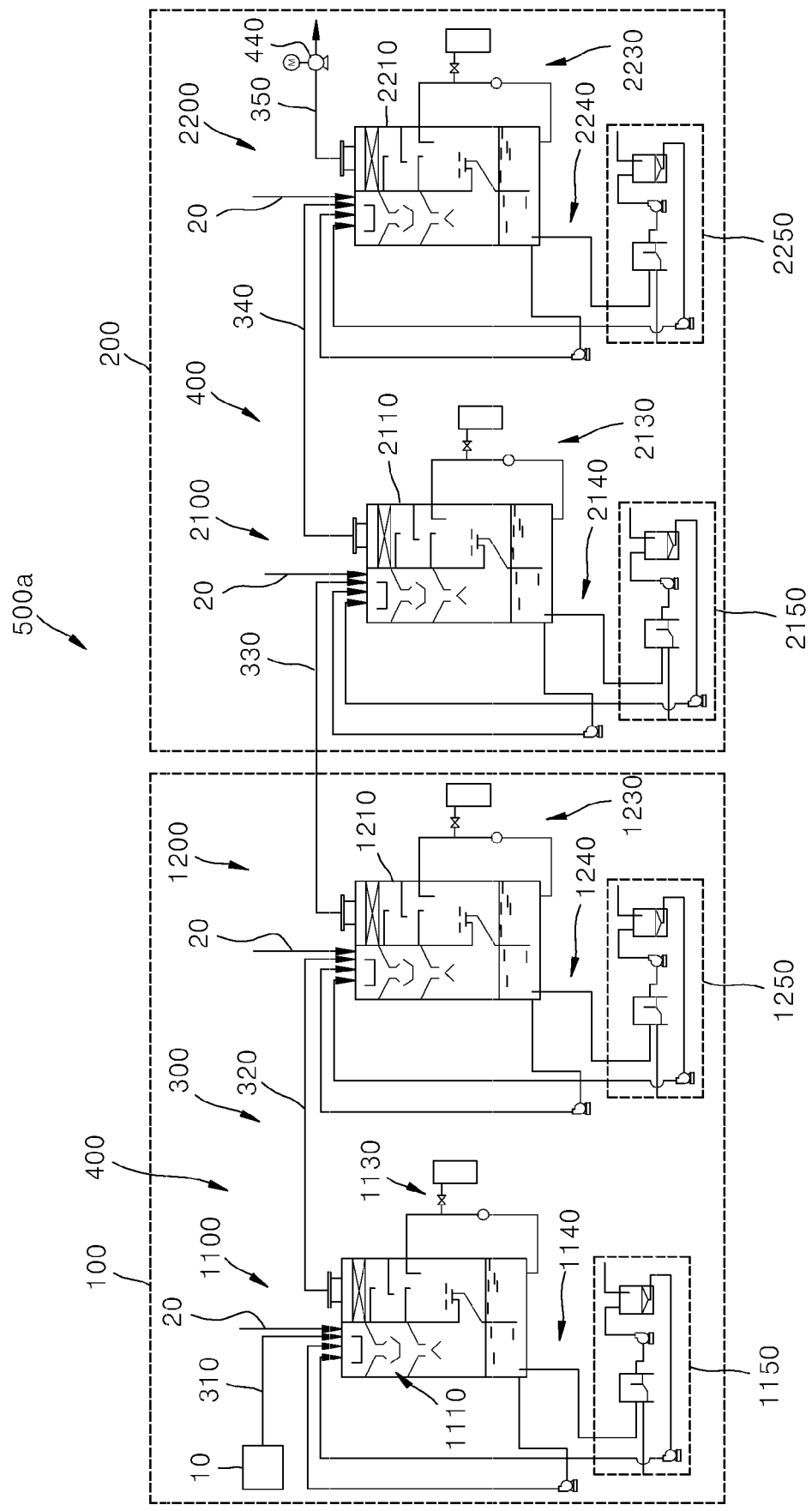
FIG. 3 is a view of complex malodor removing equipment of FIG. 1, according to another embodiment of the present invention.

Referring to FIG. 3, in complex malodor removing equipment 500*a*, the fourth suction fan 440 may be installed only on the discharge line 350. In this case, the capacity of the fourth suction fan 440 may be increased so that the inside of the neutralizing module 100 and the balancing module 200 is in the negative pressure state, and a damper etc. may be installed to reinforce the negative pressure of the neutralizing module 100 at a front end of the complex malodor removing equipment 500*a*.

Meanwhile, the suction fan 400 may operate the neutralizing module 100 and the balancing module 200 selectively in consideration of the operation and inside negative pressure state of the neutralizing module 100 and the balancing module 200 other than the above-described embodiment.

Figure 4:
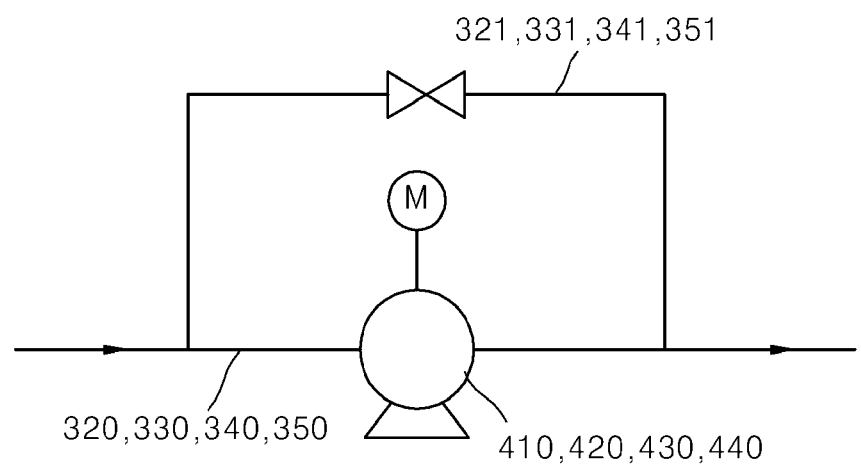
FIG. 4 is a view of the case where a bypass line is installed in the complex malodor removing equipment of FIG. 1.

Referring to FIG. 4, the gas line 300 may form a bypass line that bypasses each suction fan 400 and includes a first bypass line 321, a second bypass line 331, a third bypass line 341, and a fourth bypass line 351.

The first bypass line 321 is connected to and communicates with the first gas line 320 at front and rear ends of the first suction fan 410 so that the malodorous gas bypasses the first suction fan 410.

The second bypass line 331 is connected to and communicates with the second gas line 330 at front and rear ends of the second suction fan 420 so that the malodorous gas bypasses the second suction fan 420.

The third bypass line 341 is connected to and communicates with the third gas line 340 at front and rear ends of the third suction fan 430 so that the malodorous gas bypasses the third suction fan 430.

The fourth bypass line 351 is connected to and communicates with the discharge line 350 at front and rear ends of the fourth suction fan 440 so that the malodorous gas bypasses the fourth suction fan 440.

Meanwhile, after the malodorous gas is introduced into the acidity neutralizing module 1100, the alkaline neutralizing module 1200, the oxidation balancing module 2100 and the reduction balancing module 2200, the malodorous gas is in contact with the water so that the malodor-causing substances included in the malodorous gas are dissolved in the water, are removed and then are discharged. The acidity neutralizing module 1100, the alkaline neutralizing module 1200, the oxidation balancing module 2100, and the reduction balancing module 2200 are substantially similar to each other, and configurations thereof are also similar to each other in response to this, and the acidity neutralizing module 1100, the alkaline neutralizing module 1200, the oxidation balancing module 2100, and the reduction balancing module 2200 include a body 1110, 1210, 2110, or 2210, a malodor removing unit, a treatment liquid supply unit 1130, 1230, 2130, or 2230, a drain module 1140, 1240, 2140, or 2240, and a Venturi module 1150. Thus, hereinafter, the configuration of the acidity neutralizing module 1100 among the acidity neutralizing module 1100, the alkaline neutralizing module 1200, the oxidation balancing module 2100, and the reduction balancing module 2200 will be described.

Figure 5:
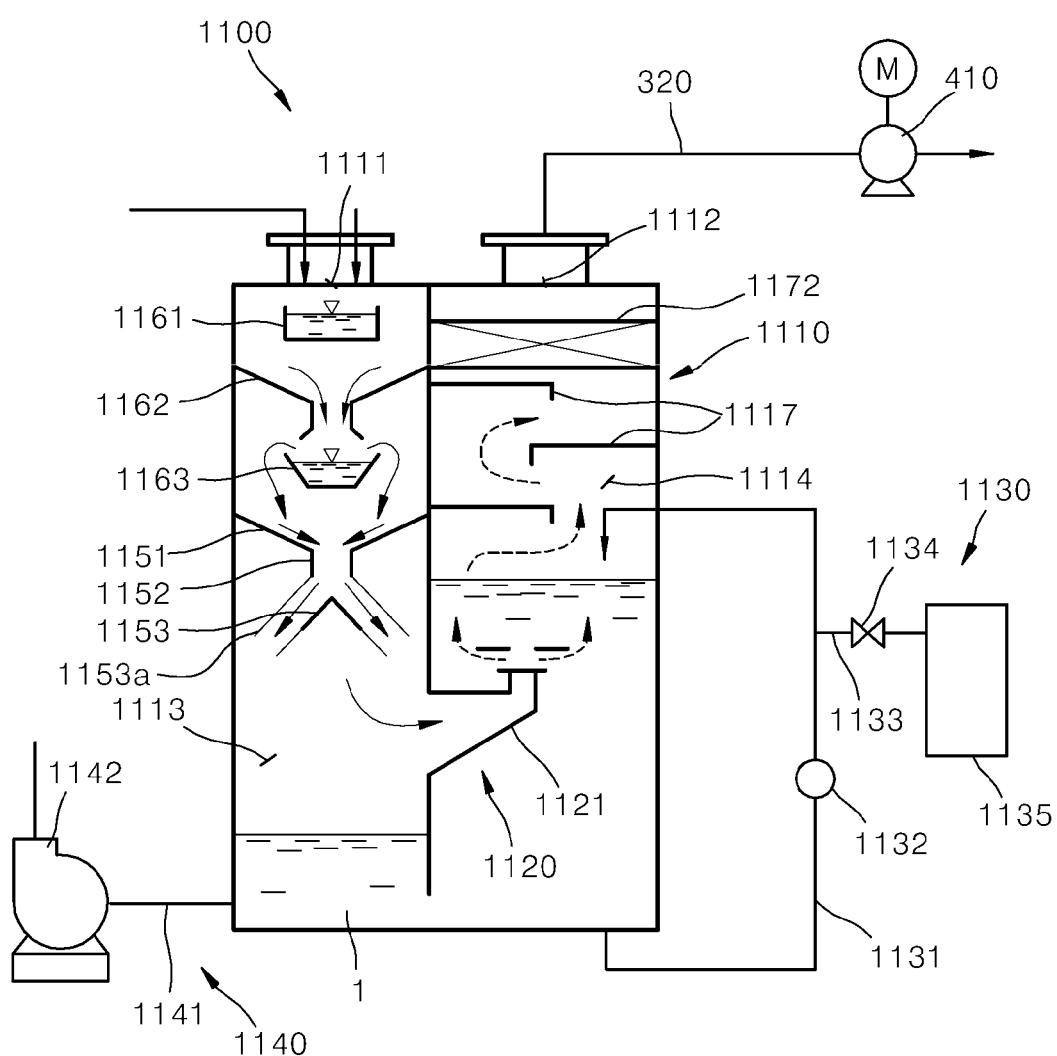
FIG. 5 is a cross-sectional view of an inside of a body of the complex malodor removing equipment of FIG. 1.

Referring to FIG. 5, the body 1110 includes an inlet into which the malodorous gas is introduced through the gas line 300, and an outlet into and from which the introduced malodorous gas is suctioned and discharged by the suction fan 400.

Also, the body 1110 has a storage space in which water used to dissolve the malodorous gas is accommodated, and the storage space includes a sub-space 1113 in which the malodorous gas is introduced from the inlet, and a main space 1114 which communicates with the sub-space 1113, into which the malodorous gas is introduced and in which the outlet is formed.

Thus, when the suction fan 400 operates, as illustrated, the body 1110 during operation has the storage space in a negative pressure state that is slightly lower than an atmospheric pressure due to a suction force of the suction fan 400. Thus, the level of the water in the storage space is increased so that an atomizing device 1120 to be described later is immersed.

Meanwhile, the complex malodor removing equipment 500 includes a fluid supply unit 10 that supplies water from an upper portion of the body 1110 into the sub-space 1113, and the fluid supply unit 10 includes a well-known fluid supply configuration having the fluid supply line 20 and a valve, and a detailed description thereof will be omitted.

The malodor removing unit is provided inside the body 1110, removes the malodor-causing substances by dissolving the malodorous gas in the water, and includes the atomizing device 1120.

The atomizing device 1120 is provided at a supply portion into which the malodorous gas of the main space 1114 of the body 1110 is introduced, refines the malodorous gas to supply the malodorous gas in the sub-space 1113 into the main space 1114, and includes a nozzle unit 1121 and a collision unit 1122.

The nozzle unit 1121 is provided at the supply port of the main space 1114 and supplies the malodorous gas, and one end of the nozzle unit 1121 protrudes to be immersed in the water having an increased level when the main space 114 is in the negative pressure state due to the suction fan 400, and a gas flow path formed inside the nozzle unit 1121, the gas flow path having a flow cross-section gradually reduced to increase a flow speed of the malodorous gas.

The nozzle unit 1121 includes an upper plate and a lower plate, and an inlet into which the water and the malodorous gas are introduced, is formed at one side of the nozzle unit 1121, and an outlet in which water is filled and from which the malodorous gas introduced through the inlet is discharged in an upward direction, is formed at the other side of the nozzle unit 1121. Here, the nozzle unit 1121 has a gas flow path that allows the inlet and the outlet to communicate with each other, formed therein. Because a passage cross-section of the outlet is smaller than a passage cross-section of the inlet, the gas flow path is formed in such a way that a discharge speed is faster than an introduction speed. Thus, the malodorous gas introduced through the inlet gets an increase in speed and is discharged.

The collision unit 1122 is placed at an upper portion of the nozzle unit 1121 and allows the malodorous gas sprayed from the nozzle unit 1121 to collide with the collision unit 1122 so that the malodorous gas can be refined. In detail, the collision unit 1122 has a plate shape and forms a multi-stage structure along the vertical direction and is formed as collision plates 1171 arranged in a horizontal direction with respect to the discharge direction of the malodorous gas, and the collision unit 1122 is spaced from one end of the nozzle unit 1121, the discharged malodorous gas collides with a bottom surface and is dispersed laterally so that the malodorous gas can be refined. Here, in the collision unit 1122, a plurality of collision plates 1171 are stacked to be spaced apart from one another in the vertical direction so that refinement of the malodorous gas can be further promoted.

Meanwhile, an operation of the above-described atomizing device 1120 will be described. When the operation of the atomizing device 1120 stops, the level of water is lowered so that the water is filled in the nozzle unit 1121. However, during an operation of the atomizing device 1120, the storage space is in the negative pressure state, and water in the nozzle unit 1121 flows into the storage space, and the level of water in the storage space is increased so that the collision unit 1122 is immersed in the water. In this way, in a state in which the collision unit 1122 is immersed in the water, the malodorous gas gets an increase in speed due to the nozzle unit 1121, flows, and then is refined by the collision unit 1122 in the water.

The malodorous gas is in contact with the water in the storage space, the malodor-causing substances are dissolved in the water and liquidity of the water is changed. In this case, the treatment liquid supply unit 1130, 1230, 2130, or 2230 neutralizes liquidity of the water based on pH concentration using the treatment liquid so that the malodor-causing substances can be continuously and effectively removed.

In detail, the treatment liquid supply unit 1130, 1230, 2130, or 2230 supplies the treatment liquid into the storage space so as to remove the malodor-causing substances dissolved in the water in the storage space based on pH concentration, and supplies the treatment liquid to a fluid circulation line 1131 to be described later so that the treatment liquid and the water can be premixed with each other and can be supplied into the storage space, and includes the fluid circulation line 1131, a circulation pump 1132, and a treatment liquid supply line 1133.

One end of the fluid circulation line 1131 is connected to a lower portion of the body 1110, and the other end of the fluid circulation line 1131 is connected to an upper portion of the body 1110 so that the water in the lower portion of the storage space can be circulated to the upper portion of the storage space.

The circulation pump 1132 is provided on the fluid circulation line 1131 to forcibly circulate the water.

One end of the treatment liquid supply line 1133 is connected to the fluid circulation line 1131 at downstream of a supply pump, and the other end of the treatment liquid supply line 1133 is connected to a treatment liquid storage tank 1135 in which the treatment liquid is stored, so that the treatment liquid can be supplied to the fluid circulation line 1131. In this case, the treatment liquid supply unit 1130, 1230, 2130, or 2230 includes a regulating valve 1134 that is provided on the treatment liquid supply line 1133 and adjusts the supply amount of the treatment liquid.

Meanwhile, the treatment liquid supply line 1133 supplies different treatment liquids to the acidity neutralizing module 1100, the alkaline neutralizing module 1200, the oxidation balancing module 2100, and the reduction balancing module 2200, respectively, so that the malodor-causing substances having different properties can be removed. This will be described below.

First, the acidity neutralizing module 1100 neutralizes the water having acidity due to an acidic malodor-causing substance such as hydrogen sulphide dissolved in the water and supplies acidity neutralizing treatment liquid including alkaline substances to the fluid circulation line 1131 as components for neutralizing the water having acidity. In this case, the acidity neutralizing treatment liquid may be one selected from the group consisting of an aqueous sodium hydroxide (NaOH) solution, an aqueous calcium hydroxide $(Ca(OH)_2)$ solution, and an aqueous magnesium hydroxide $(Mg(OH)_2)$ solution. However, embodiments of the present disclosure are not limited thereto.

The alkaline neutralizing module 1200 neutralizes the water having alkalinity caused by an alkaline malodor-causing substances, such as ammonia or trimethylamine in the malodorous gas, dissolved in the water, and supplies an alkaline neutralizing treatment liquid including acidity substances in the water to the fluid circulation line 1131. Here, the alkaline neutralizing treatment liquid may be one selected from the group consisting of an aqueous sulfuric acid $(H_2SO_4)$ solution, an aqueous hydrochloric acid (HCl) solution, and an aqueous phosphoric acid $(H_3PO_4)$ solution.

The oxidation balancing module 2100 oxidizes and decomposes the water in which a neutral malodor-causing substance, such as acetaldehyde, methyl sulphide, dimethyl disulphide, or methyl mercaptan in the malodorous gas, is dissolved, and supplies an oxidation treatment liquid including an oxidizing agent to the fluid circulation line 1131 so as to balance the water. Here, the oxidation treatment liquid may be an aqueous hypochlorous acid (HClO) solution or an aqueous sodium hypochlorite (NaOCl) solution.

The reduction balancing module 2200 supplies reducing treatment liquid including a reducing agent for reducing the water in which an oxidizing agent gas generated by the oxidizing agent of the oxidation balancing module 2100 is dissolved in water, to the fluid circulation line 1131. In this case, the reducing agent may be one selected from the group consisting of an aqueous sodium thiosulfate $(NaS_2O_3)$ solution, an aqueous sodium sulfite $(Na_2SO_3)$ solution, and an aqueous sodium bisulfite (NaHSO$_3$) solution, which have easy handling and economic feasibility.

The following Table 1 shows an example of malodor-causing substances for each of the alkaline neutralizing module 1200, the acidity neutralizing module 1100, and the oxidation balancing module 2100 (an oxidation module), treatment liquid caused thereby, and reaction formulae.

The drain line drains the water in the storage space to supply the water into the storage tank.

The control valve is installed on the drain line and controls the flow of the water. The fluid circulation unit is connected to the storage tank and the body 1110 to supply the water in the storage tank to the body 1110.

TABLE 1

| | Malodor-causing substances | Treatment liquid | Reaction formula |
|---|---|---|---|
| Alkaline neutralizing module | Ammonia trimethylamine | H$_2$SO$_4$ | 2NH$_3$ + H$_2$SO$_4$ = (NH$_4$)$_2$SO$_4$ <br> (CH$_3$)$_3$N + H$_2$SO$_4$ = (CH$_3$)$_3$N•H$_2$SO$_4$ |
| Acidity neutralizing module | Hydrogen sulfide | NaOH | H$_2$S + NaOH = Na$_2$S + H$_2$O |
| Oxidation module | Acetaldehyde <br> Methyl sulfide <br> Dimethyl disulfide <br> Methyl mercaptan | NaOCl | CH$_3$CHO + NaOCl + NaOH = CH$_3$COONa + NaCl + H$_2$O <br> (CH$_3$)$_2$S + 3NaOCl = (CH$_3$)$_2$SO$_3$ + 3NaCl <br> (CH$_3$)$_2$S + 2NaOCl = (CH$_3$)$_2$S$_2$O$_2$ + 2NaCl <br> CH$_3$SH + 3NaOCl = CH$_3$SO$_3$H + 3NaCl |

In the complex malodor removing equipment 500, when an initial malodorous gas and the inflow amount of the malodor-causing substances within the malodorous gas are measured by a flow sensor or a pH sensor, although not shown, the malodor treating units may supply the treatment liquid according to the supply amount of the treatment liquid with respect to the amount of malodor-causing substances previously calculated based on the measured initial malodorous gas and inflow amount of the malodor-causing substances.

Meanwhile, in the complex malodor removing equipment 500, a worker may stop an operation of the acidity neutralizing module 1100, the alkaline neutralizing module 1200, the oxidation balancing module 2100, and the reduction balancing module 2200, respectively, or may operate the acidity neutralizing module 1100, the alkaline neutralizing module 1200, the oxidation balancing module 2100, and the reduction balancing module 2200, respectively, selectively in response to the malodorous gas. However, the complex malodor removing equipment 500 may control the acidity neutralizing module 1100, the alkaline neutralizing module 1200, the oxidation balancing module 2100, and the reduction balancing module 2200, respectively, using a controller.

In this case, the complex malodor removing equipment 500 may connect the suction fan 400, the regulating valve 1134 of the treatment liquid supply unit 1130, 1230, 2130, or 2230, the pH sensor and a pressure sensor installed in the body 1110, and the controller to one another. The controller may control the negative pressure state of the body 1110 and the supply of the treatment liquid by operating the suction fan 400 in response to information of the pH sensor and the pressure sensor.

In the complex malodor removing equipment 500, preferably, water having easy handling and economic feasibility is used as water used to dissolve the malodor-causing substances. However, various types of water such as oil, instead of the water may be used, and the malodorous gas includes various types of malodorous gases including malodorous gas generated when food wastes are treated, and malodorous gas generated in a night soil treatment plant, a livestock shed, a sewage treatment plant, and the like.

The drain module 1140, 1240, 2140, or 2240 drains the water in the storage space and includes a drain line 1141, a control valve (not shown), and a fluid circulation unit 1142.

The Venturi module 1150 is installed in the sub-space 1113, accelerates the introduced water and the malodorous gas together, allows the water and the malodorous gas to be in contact with each other, and removes the malodor-causing substances.

In detail, the Venturi module 1150 includes a funnel unit 1151, a discharge unit 1152, and a collision part 1153. The upper portion of the funnel unit 1151 is opened so that the malodorous gas and the water are introduced into the funnel unit 1151, and the funnel unit 1151 has a tapered shape in which a diameter thereof is gradually decreased as getting to a lower portion thereof, such that flow velocity of the water and the malodorous gas can be increased.

The discharge unit 1152 extends from a discharge port of the funnel unit 1151 from which the water and the malodorous gas are gathered and discharged downwards, in a downward direction to guide the water and the malodorous gas downwards.

The collision part 1153 is spaced apart a lower portion of the discharge unit 1152, allows the water discharged from the discharge unit 1152 to collide with a top surface and to be dispersed laterally, thereby forming a fluid shielding layer 1153$a$ and allowing the malodor-causing substances to be in contact with the fluid shielding layer 1153$a$.

Furthermore, the complex malodor removing equipment 500 further includes a water tank 1161, a water current plate 1162, a shielding plate 1117, and an eliminator 1172, which are installed in the body 1110.

The water tank 1161 is installed within the sub-space 1113 and is spaced from the upper portion of the Venturi module 1150, and the upper portion of the water tank 1161 is opened such that upward-transferred water can be dropped and stored in the water tank 1161.

The water current plate 1162 is spaced from the lower portion of the water tank 1161, is spaced apart from the upper portion of the Venturi module 1150, has a tapered shape in which the water overflowing from the water tank 1161 is introduced and a diameter of the water current plate 1162 is gradually decreased as getting closer to a lower portion of the water current plate 1162, such that the water is gathered and is discharged to a water current discharge port formed at a bottom end of the water current plate 1162. Meanwhile, a mixture tube 1163 in which the water overflowing from the water current plate 1162 and the malodorous gas are mixed and stored, is placed at the lower portion of the water current plate 1162.

A plurality of shielding plates 1117 are arranged in the body 1110 of an upper side of the atomizing device 1120 to cross one another and to be spaced apart one another and are arranged in the form of a plate in a latitudinal direction, such that the malodorous gas discharged from the atomizing device 1120 collides with the plurality of shielding plates 1117 and is refined.

The eliminator 1172 includes a stainless room, or the like and removes moisture contained in the malodorous gas.

Furthermore, the complex malodor removing equipment 500 includes a sludge discharge unit 1150, 1250, 2150, or 2250 that is placed at a lower portion of the body 1110 and discharges sludge in the storage space. The sludge discharge unit 1150, 1250, 2150, or 2250 may include a water discharge line, which communicates with the lower portion of the body 1110 and through sludge gathered in the lower portion of the storage space is discharged, a sump, which is connected to the water discharge line and in which the sludge is stored, and a water discharge valve provided on the water discharge line, and water in the sump is re-circulated and is supplied into the storage space.

Also, the complex malodor removing equipment 500 may further include a filtering unit on the discharge line 350. The filtering unit may remove malodor-causing substances that remain in the malodorous gas. The filtering unit may be various elements that may adsorb or remove the remaining malodor, such as a charcoal adsorption top in which activated carbon is placed.

Figure 6:
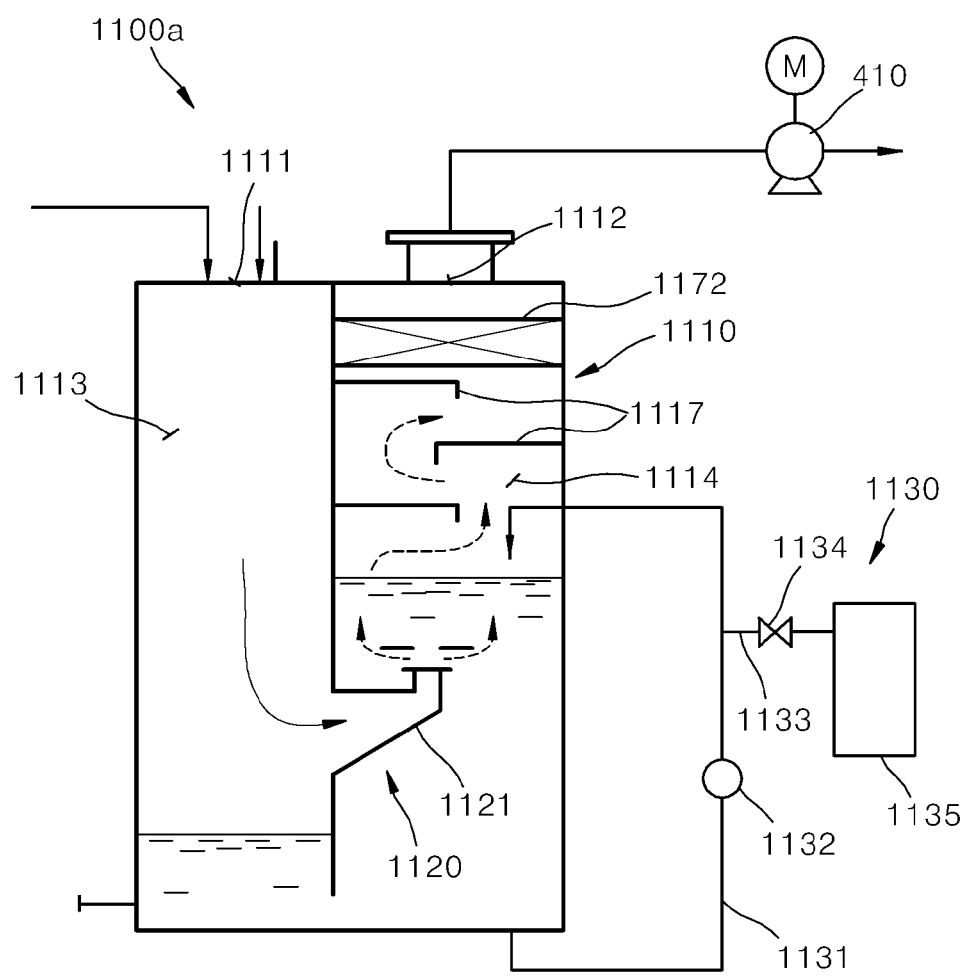
FIG. 6 is a cross-sectional view of a body of a neutralizing module and a balancing module of FIG. 1, according to another embodiment of the present invention.
Figure 7:
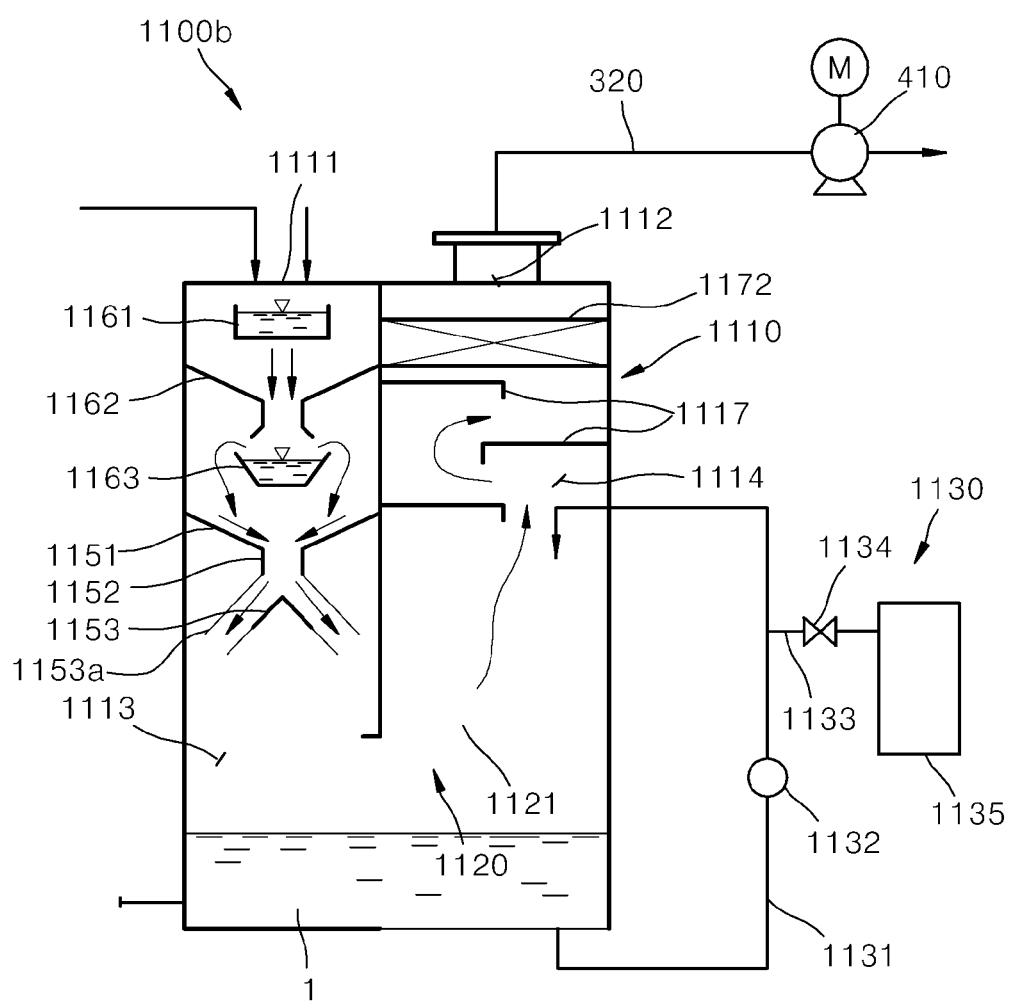
FIG. 7 is a cross-sectional view of a body of a neutralizing module and a balancing module of FIG. 1, according to another embodiment of the present invention.
Figure 8:
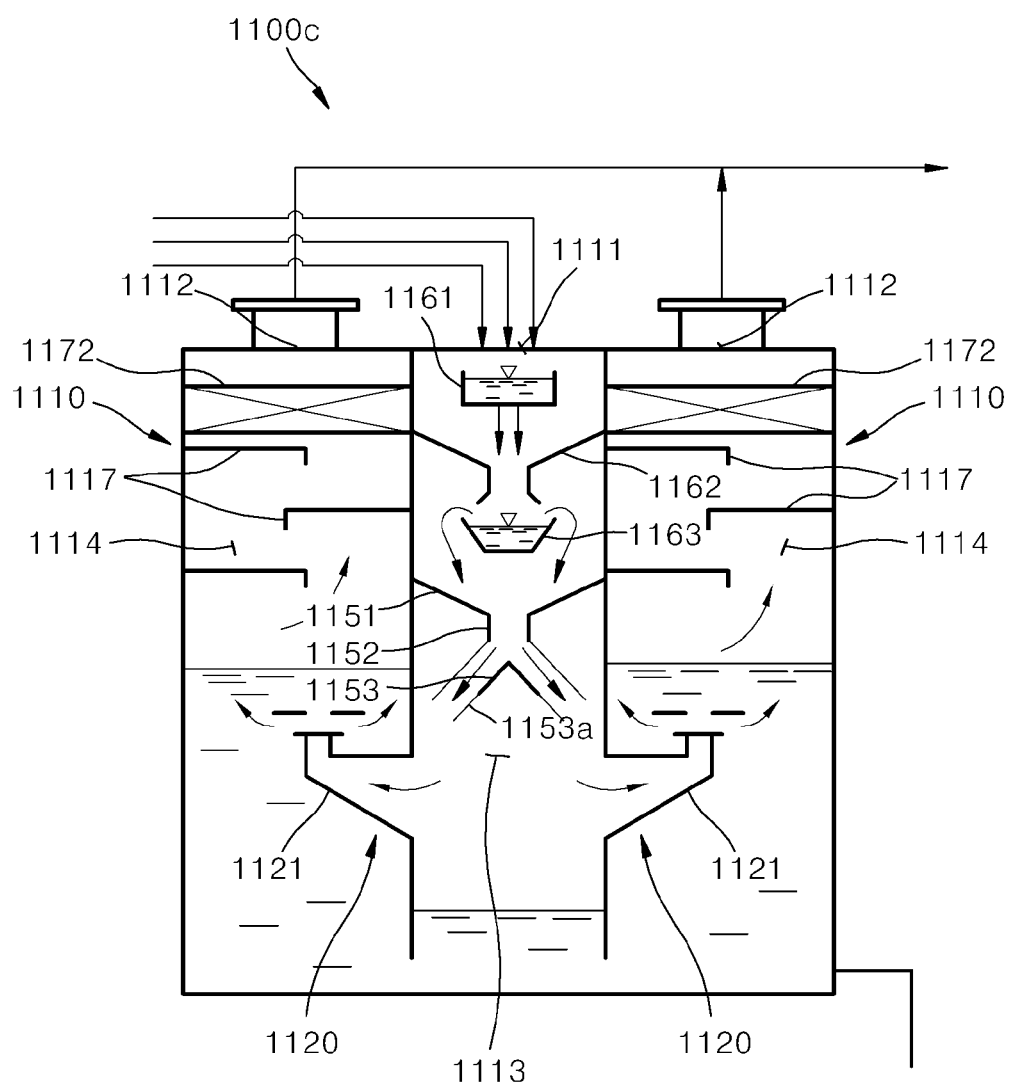
FIG. 8 is a cross-sectional view of a body of a neutralizing module and a balancing module of FIG. 1, according to another embodiment of the present invention.

FIGS. 6 through 8 illustrate other embodiments of the body 1110. First, referring to FIG. 6, the body 1110*a* is configured in such a way that the malodorous gas passes through the malodor removing unit without passing through the elements such as the Venturi module 1150 and the water tank 1161, without elements including the Venturi module 1150, the water bank 1161 and the water current plate 1162 in the sub-space 1113, in comparison with FIG. 1.

Next, referring to FIG. 7, a body 1110*b* is configured in such a way that it does not include the atomizing device 1120 as the malodor removing unit within the main space 1114 in comparison with FIG. 1, the introduced malodorous gas passes through the water tank 1161 and the Venturi module 1150 and then passes through the shielding plates 1117 and the eliminator 1172.

Referring to FIG. 8, a body 1110*c* includes one-sub space 1113 and a pair of main spaces 1114 that communicate with both sides of the sub-space 1113. When the malodorous gas is introduced into the sub-space 1113 at a center thereof, the malodorous gas is discharged into the both-side main spaces 1114, and the malodorous gas discharged from the pair of main spaces 1114 is gathered again and flows. Here, like reference numerals represent like elements.

As described above, the body may include various elements such as the Venturi module 1150, the water tank 1161, the water current plate 1162, and the malodor removing unit, which are installed in the body, selectively in response to the malodorous gas, and a structure of the body may be designed in various ways.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, the present invention can be used in malodor removing equipment for removing malodor discharged from the malodor removing equipment.

The invention claimed is:

1. A complex malodor removing equipment comprising:
a neutralizing module which dissolves a portion of malodor-causing substances, in malodorous gas introduced from malodor-producing equipment, in liquid water and removes same, which includes an acidity neutralizing module that introduces an alkaline substance from outside and removes an acidic malodor-causing substance from the malodor-causing substances in order to neutralize same, and an alkaline neutralizing module that introduces an acidic substance from outside and removes an alkaline malodor-causing substance from the malodor-causing substances in order to neutralize same, and which connects the acidity neutralizing module and the alkaline neutralizing module in response to the malodorous gas and operates the acidity neutralizing module and the alkaline neutralizing module; and
a balancing module which dissolves the remainder of the malodor-causing substances, in the malodorous gas introduced from the neutralizing module, in water and removes same, which includes an oxidation balancing module that introduces an oxidizing agent from outside and balances the malodor-causing substances in order to oxidize same, and a reduction balancing module that introduces a reducing agent from outside and balances the malodor-causing substances in order to reduce same, and which connects the oxidation balancing module and the reduction balancing module in response to the malodorous gas and operates the oxidation balancing module and the reduction balancing module.

2. The complex malodor removing equipment of claim 1, wherein the
neutralizing module selectively operates the acidity neutralizing module and the alkaline neutralizing module in response to the malodorous gas, and the balancing module selectively operates the oxidation balancing module and the reduction balancing module in response to the malodorous gas.

3. The complex malodor removing equipment of claim 1, wherein the
neutralizing module serially-connects the acidity neutralizing module to the alkaline neutralizing module sequentially in an order of the acidity neutralizing module and the alkaline neutralizing module, and the balancing module serially-connects the oxidation balancing module to the reduction balancing module sequentially in an order of the oxidation balancing module to the reduction balancing module.

4. The complex malodor removing equipment of claim 1, further comprising a suction fan, which is provided on a gas line in which the malodorous gas of the neutralizing module and the balancing module flows, which suctions the malodorous gas within the neutralizing module and the balancing module and flows same and allows the inside of the neutralizing module and the balancing module in a negative pressure state.

5. The complex malodor removing equipment of claim 4, wherein the gas line comprises a supply line through which the malodorous gas is introduced from the malodor-producing equipment and which supplies the malodorous gas to the neutralizing module, a first gas line that connects the acidity neutralizing module and the alkaline neutralizing module within the neutralizing module to each other, a second gas line that connects the neutralizing module to the balancing module, a third gas line that connects the oxidation balancing module and the reduction balancing module within the balancing module to each other, and a discharge line, which is connected to a discharge port of the balancing module, and the suction fan is provided on the discharge line.

6. The complex malodor removing equipment of claim 4, wherein the gas line comprises a supply line through which the malodorous gas is introduced from the malodor-producing equipment and which supplies the malodorous gas to the neutralizing module, a first gas line that connects the acidity neutralizing module and the alkaline neutralizing module within the neutralizing module to each other, a second gas line that connects the neutralizing module to the balancing module, a third gas line that connects the oxidation balancing module and the reduction balancing module within the balancing module to each other, and a discharge line connected to a discharge port of the balancing module, and the suction fan comprises a first suction fan installed on the first gas line, a second suction fan installed on the second gas line, a third suction fan installed on the third gas line, and a fourth suction fan installed on the discharge line.

7. The complex malodor removing equipment of claim 6, wherein the gas line comprises:

a first bypass line connected to and communicating with the first gas line at front and rear ends of the first suction fan so that the malodorous gas bypasses the first suction fan;

a second bypass line connected to and communicating with the second gas line at front and rear ends of the second suction fan so that the malodorous gas bypasses the second suction fan; and a third bypass line connected to and communicating with the third gas line at front and rear ends of the third suction fan so that the malodorous gas bypasses the third suction fan.

8. The complex malodor removing equipment of claim 4, wherein each of the oxidation neutralizing module, the alkaline neutralizing module, the oxidation balancing module, and the reduction balancing module comprises:

a body including an inlet into which the malodorous gas is introduced, and an outlet from which the introduced malodorous gas is suctioned and discharged, formed therein, an inside of the body including a sub-space into which the malodorous gas is introduced from the inlet, a main space, which communicates with the sub-space and into which the malodorous gas is introduced and in which the outlet is formed, and a storage space in which the water used to dissolve the malodorous gas is accommodated; and a malodor removing unit placed inside the body and removing the malodor-causing substances by dissolving the malodorous gas in the water.

9. The complex malodor removing equipment of claim 8, wherein the malodor removing unit comprises an atomizing device including a nozzle unit provided at a supply port of the main space and supplying the malodorous gas, one end of the nozzle unit protruding to be immersed in the water having an increased level when the main space is in the negative pressure state due to the suction fan, and a gas flow path formed inside the nozzle unit, the gas flow path having a flow cross-section gradually reduced to increase a flow speed of the malodorous gas, and a collision unit provided at one end of the nozzle unit, allowing the malodorous gas sprayed from the nozzle unit to collide with the collision unit so that the malodorous gas is refined.

10. The complex malodor removing equipment of claim 8, wherein each of the acidity neutralizing module, the alkaline neutralizing module, the oxidation balancing module, and the reduction balancing module comprises a treatment liquid supply unit configured to supply treatment liquid into the storage space so that the malodor-causing substances dissolved in the water in the storage space are removed based on pH concentration.

11. The complex malodor removing equipment of claim 10, wherein the treatment liquid supply unit comprises:

a fluid circulation line having one end connected to a lower portion of the body and the other end connected to an upper portion of the body so that the water in the lower portion of the storage space is circulated to the upper portion of the storage space;

a circulation pump provided on the fluid circulation line; and a treatment liquid supply line having one end connected to the fluid circulation line at downstream of a circulation pump and configured to supply the treatment liquid to the fluid circulation line.

12. The complex malodor removing equipment of claim 11, wherein the acidity neutralizing module supplies acidic neutralizing treatment liquid including alkaline substances for neutralizing the water having acidity due to an acidic malodor-causing substance dissolved in the water to the fluid circulation line, and the acidity neutralizing treatment liquid is one selected from the group consisting of an aqueous sodium hydroxide (NaOH) solution, an aqueous calcium hydroxide $(Ca(OH)_2)$ solution, and an aqueous magnesium hydroxide $(Mg(OH)_2)$ solution.

13. The complex malodor removing equipment of claim 11, wherein the alkaline neutralizing module supplies alkaline neutralizing treatment liquid including acid substances for neutralizing the water having alkalinity due to an alkaline malodor-causing substance dissolved in the water to the fluid circulation line, and the alkaline neutralizing treatment liquid is one selected from the group consisting of an aqueous sulfuric acid $(H_2SO_4)$ solution, an aqueous hydrochloric acid (HCl) solution, and an aqueous phosphoric acid $(H_3PO_4)$ solution.

14. The complex malodor removing equipment of claim 11, wherein the oxidation balancing modules supplies oxidation treatment liquid including an oxidizing agent for oxidizing and decomposing the water in which a neutral malodor-causing substance is dissolved, to the fluid circulation line, and the oxidation treatment liquid comprises an aqueous hypochlorous acid (HOCl) solution or an aqueous sodium hypochlorite (NaOCl) solution.

15. The complex malodor removing equipment of claim 11, wherein the reduction balancing module supplies reducing treatment liquid including a reducing agent for reducing the water in which an oxidizing agent is generated by the oxidizing agent of the oxidation balancing module, to the fluid circulation line, and the reducing agent is one selected from the group consisting of an aqueous sodium thiosulfate (NaS2O3) solution, an aqueous sodium sulfite (Na2SO3) solution, and an aqueous sodium bisulfite (NaHSO3) solution.

16. A complex malodor removing equipment comprising:

a neutralizing module which dissolves a portion of malodor-causing substances, in malodorous gas introduced from malodor-producing equipment, in liquid water and removes same, and which removes the portion of the malodor-causing substances by introducing an acidic substance or an alkaline substance into the malodorous gas from outside, using a neutralizing reaction; and a balancing module which is placed at downstream of the neutralizing module with respect to a flow direction of the malodorous gas and removes a portion of the malodor-causing substances by introducing a reducing agent or an oxidizing agent into the malodorous gas from outside, using a reduction reaction or an oxidation reaction, wherein the neutralizing module comprises:
- an alkaline neutralizing module which introduces an acidic substance from outside and removes an alkaline malodor-causing substance from the malodor-causing substances introduced from the malodor-producing equipment in order to neutralize same; and
- an acidity neutralizing module which is placed at downstream of the alkaline neutralizing module, introduces an alkaline substance from outside and removes an acidic malodor-causing substance discharged while not being removed by the alkaline neutralizing module, from the malodor-causing substances in order to neutralize same, and the complex malodor removing equipment further comprising a suction fan, which is provided on a gas line in which the malodorous gas passes through the balancing module and is discharged and which allows the inside of the alkaline neutralizing module, the acidity neutralizing module and the balancing module in a negative pressure state.

17. The complex malodor removing equipment of claim 16, wherein the balancing module comprises an oxidation balancing module which dissolves the malodor-causing substances, in the malodorous gas introduced from the neutralizing module, in water and removes same, and which removes same by introducing an oxidizing agent from outside in order to oxidize the malodor-causing substances.

18. The complex malodor removing equipment of claim 16, wherein the balancing module comprises:
- an oxidation balancing module which dissolves the malodor-causing substances, in the malodorous gas introduced from the neutralizing module, in water and removes same, and which removes same by introducing an oxidizing agent from outside in order to oxidize the malodor-causing substances; and
- a reduction balancing module which dissolves the malodor-causing substances, in the malodorous gas introduced from the acidity balancing module, in water and removes same, and which removes same by introducing a reducing agent from outside in order to reduce the malodor-causing substances.

19. The complex malodor removing equipment of claim 16, wherein the balancing module comprises a reduction balancing module which dissolves the malodor-causing substances, in the malodorous gas introduced from the neutralizing module, in water and removes same, and which removes same by introducing a reducing agent from outside in order to reduce the malodor-causing substances.

20. A complex malodor removing equipment comprising:
- a neutralizing module comprising an alkaline neutralizing module which introduces an acidic substance from outside and removes an alkaline malodor-causing substance from malodor-causing substances, in malodorous gas introduced from malodor-producing equipment, in order to neutralize same and an acidity neutralizing module which is placed at downstream of the alkaline neutralizing module, introduces an alkaline substance from outside and removes an acidic malodor-causing substance from the malodor-causing substances, in the malodorous gas in order to neutralize same; and
- a balancing module which is placed at downstream of the neutralizing module with respect to a flow direction of the malodorous gas and comprises an oxidation balancing module which removes a portion of the malodor-causing substances by introducing an oxidizing agent into the malodorous gas from outside, using an oxidation reaction and a reduction balancing module which is placed at downstream of the oxidation balancing module and removes a portion of the malodor-causing substances by introducing a reducing agent into the malodorous gas from outside, using a reduction reaction.

* * * * *